United States Patent [19]
Ruderian

[11] Patent Number: 4,653,494
[45] Date of Patent: Mar. 31, 1987

[54] NASAL INHALATION SYSTEM

[76] Inventor: Max J. Ruderian, 545 Hanley Ave., Los Angeles, Calif. 90049

[21] Appl. No.: 811,279

[22] Filed: Dec. 20, 1985

[51] Int. Cl.⁴ .......................................... A61M 15/00
[52] U.S. Cl. ........................ 128/203.22; 128/204.13; 128/909; 128/203.27
[58] Field of Search ....................... 128/203.21, 203.22, 128/203.23, 203.24, 204.13, 204.17, 207.18, 909, 203.15, 200.19, 203.27, 202.21, 203.12

[56] References Cited

U.S. PATENT DOCUMENTS

| | | | |
|---|---|---|---|
| Re. 29,613 | 4/1978 | Kropfhammer | 128/909 |
| 736,111 | 8/1903 | Kautz | 128/203.27 |
| 795,866 | 8/1905 | Spanogle | 128/203.24 |
| 1,643,983 | 10/1927 | Cristina . | |
| 1,740,083 | 12/1929 | Galvin . | |
| 1,775,947 | 9/1930 | Robinson . | |
| 1,819,123 | 8/1931 | Robinson | 128/203.27 |
| 1,911,468 | 5/1933 | Robinson | 128/203.27 |
| 1,986,247 | 1/1935 | Borden | 128/203.22 |
| 2,118,327 | 5/1938 | Roberts . | |
| 2,136,844 | 11/1938 | Fair et al. | 128/203.22 |
| 2,199,724 | 5/1940 | Herbert . | |
| 2,226,582 | 12/1940 | Robinson | 128/203.27 |
| 2,426,281 | 8/1947 | Oakes | 128/204.13 |
| 2,451,540 | 10/1948 | Dinyer | 128/204.13 |
| 3,902,486 | 9/1975 | Guichard . | |
| 3,949,751 | 4/1976 | Birch et al. | 128/203.15 |
| 4,011,864 | 3/1977 | Guichard . | |
| 4,013,075 | 3/1977 | Cocozza | 128/203.15 |
| 4,016,878 | 4/1977 | Castel et al. . | |
| 4,319,566 | 3/1982 | Hayward et al. . | |
| 4,369,777 | 1/1983 | Lwoff et al. . | |
| 4,401,114 | 8/1983 | Lwoff et al. . | |

FOREIGN PATENT DOCUMENTS

| | | | |
|---|---|---|---|
| 718287 | 11/1954 | United Kingdom | 128/204.13 |

Primary Examiner—Henry J. Recla
Attorney, Agent, or Firm—Kelly, Bauersfeld & Lowry

[57] ABSTRACT

An improved nasal inhalation system is provided for vaporizing a selected medicament or the like and for convenient inhalation of the resultant vapors. In one form, the inhalation system comprises a nozzle mounted at the discharge end of a source of air flow, preferably a heated air flow, wherein the nozzle is shaped to support a medicament-containing inhaler tube for flow-through passage of the air flow to produce medicinal vapors. A conveniently sterilizable vented adapter sleeve may be carried about the inhaler tube and/or mounted on the nozzle to prevent human contact with the inhaler tube and to limit the quantitative air flow to a person's nostrils. In an alternative form, a plurality of inhaler tubes are supported within a turret assembly mounted at the discharge end of the air flow source and rotatable to align a selected one of the inhaler tubes with an open discharge tube thereby permitting flow-through passage of air.

23 Claims, 10 Drawing Figures

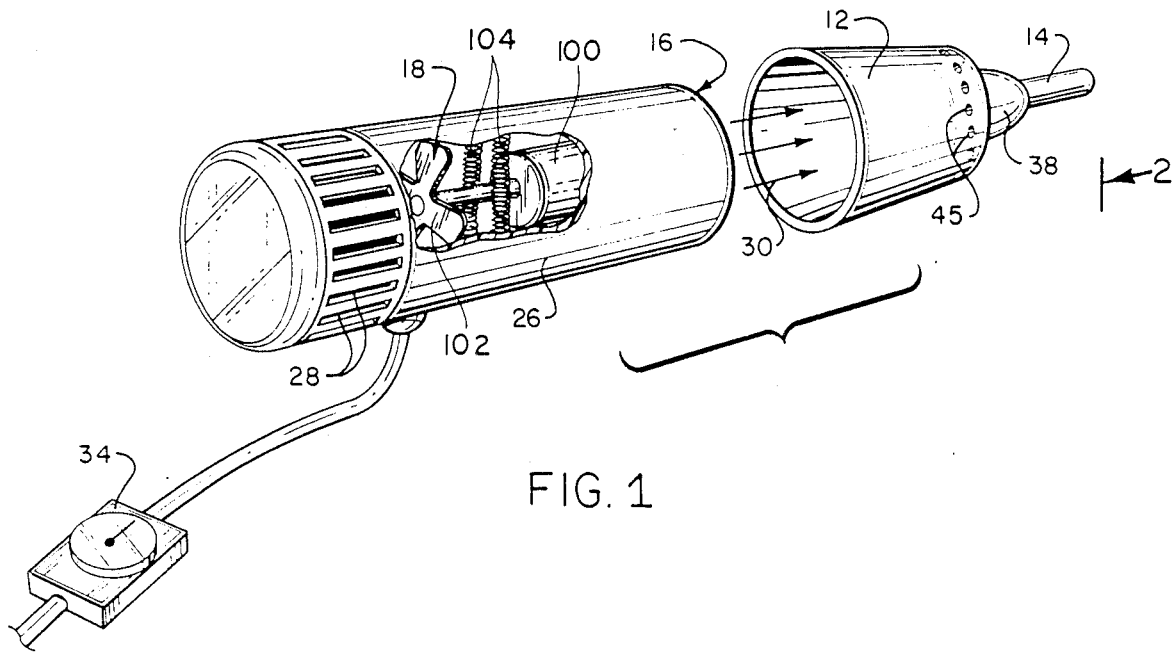
FIG. 1
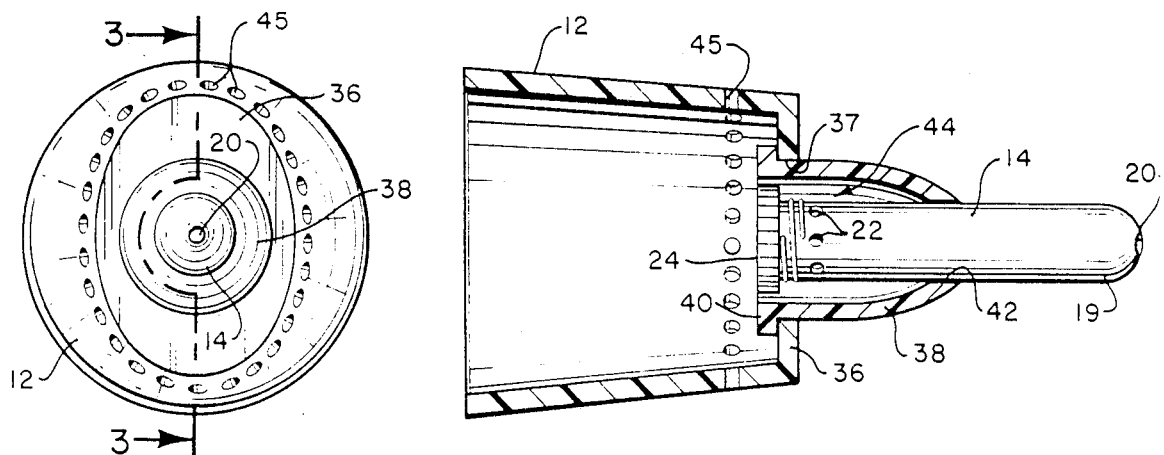
FIG. 2
FIG. 3
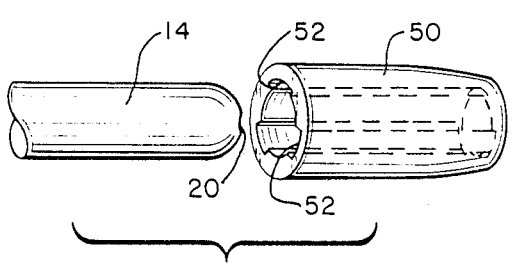
FIG. 4
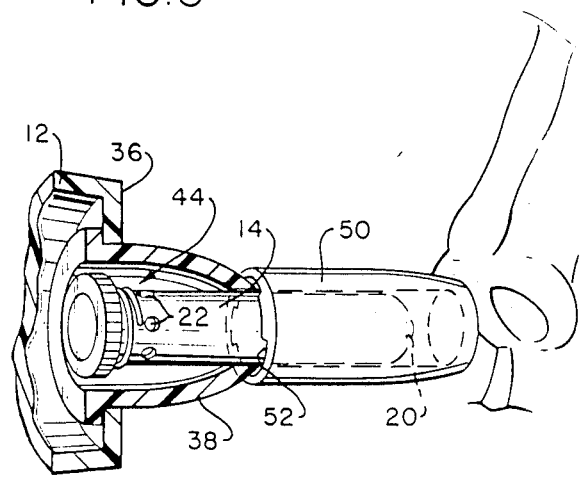
FIG. 5

NASAL INHALATION SYSTEM

BACKGROUND OF THE INVENTION

This invention discloses and claims subject matter related to applicant's copending U.S. application Ser. Nos. 683,598, filed Dec. 19, 1984; 685,831, filed Dec. 24, 1984; and 686,430, filed Dec. 26, 1984.

This invention relates generally to devices for producing medicinal vapors which can be inhaled for treatment purposes, for example, relief of nasal congestion. More particularly, this invention relates to an improved nasal inhalation system designed for supporting a conventional medicament-containing inhaler tube in a position for flow-through passage of air to produce medicinal vapors and the like.

Inhalation of medicinal vapors is known in the art as a therapeutic procedure for treatment of a variety of medical conditions. For example, medicines, such as antihistamines and the like have been used for many years in droplet or vapor form to relieve sinus congestion. More recently, it has been recognized that a wide variety of other medicines such as insulin and the like can be administered to a patient in vapor form by means of nasal inhalation. Alternately, in some instances, it may be desirable to form vapors carrying a selected fragrance which may be unrelated to medicinal applications. In accordance with one common administration technique, the medicine or fragrance-bearing substance is supported within a so-called inhaler tube designed for flow-through passage of air to produce the desired vapors which can be inhaled directly into a person's nostrils. Inhaler tubes of this type are sold, for example, by Richardson-Vicks, Inc., Wilton, Conn., under the name VICKS.

In some applications, it is desirable to provide a relatively high flow of medicinal vapors in excess of the flow obtainable by use of a conventional inhaler tube. Such devices have been proposed, for example, to include a power-driven air flow source or the like, as disclosed in applicant's above-referenced copending applications. However, prior inhalation system devices have not been adapted for use with conventional inhaler tubes but instead have required use of the medicament in some other form.

There exists, therefore, a signifcant need for an improved nasal inhalation system adapted for use with a conventional medicament-containing inhaler tube, particularly wherein the inhaler tube can be installed and/or removed from the inhalation system quickly, easily, and in a highly sanitary manner. The present invention fulfills these needs and provides further related advantages.

SUMMARY OF THE INVENTION

In accordance with the invention, an improved nasal inhalation system is provided for quickly and easily mounting a conventional nasal inhaler tube in a position for flow-through passage of air from a power-driven air source and for convenient inhalation of the medicinal or other vapors produced thereby.

In one preferred form, the improved inhalation system comprises a generally cup-shaped mounting base for removable mounting onto the discharge end of the power-driven air source, which preferably includes means for heating the air, to receive the air flow discharged therefrom. The mounting base includes a downstream end wall carrying an open nozzle having a size and shape for supporting a conventional medicament-containing inhaler tube. The nozzle has a shape converging toward its downstream end to define an air flow clearance chamber between the upstream end of the nozzle and the base end of the inhaler tube, thereby permitting air flow into the nozzle annularly about the inhaler tube base end for entry into the inhaler tube via circumferentially open inlet ports and flow-through passage for discharge through an inhaler tube exit port at the downstream end tip disposed outside the nozzle.

An adapter sleeve is provided and may be carried removably or fixed about the downstream end tip of the inhaler tube. The adapter sleeve has a length protruding beyond the exit port of the inhaler tube to prevent direct human contact with the inhaler tube. In addition, the adapter sleeve is provided with vent means for exhausting a portion of the air flow in a direction away from a person's nostril to quantitatively limit the air flow available for passage into the nostril.

In a modified form of the invention, a plurality of inhaler tubes are carried by a cup-shaped mounting base sized for removable connection onto the discharge end of an air flow source, wherein the mounting base comprises part of a turret assembly. These inhaler tubes protrude into a rotatable turret cap having an open discharge tube for alignment with a selected one of the inhaler tubes and seal means for closing off the exit ports of the remaining inhaler tubes. The turret cap is rotatably supported on the mounting base and is associated with detented index means for accommodating cap rotation moving the discharge tube into alignment with the exit port of a selected one of the inhaler tubes thereby permitting air flow passage through the selected inhaler tube. Air flow passage may be permitted through an alternate inhaler tube upon appropriate rotation of the turret cap to an alternate position.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is an exploded and partially fragmented perspective view illustrating one preferred form for an improved nasal inhalation system embodying the novel features of the invention;

FIG. 2 is a front end elevation view taken generally on the line 2—2 of FIG. 1;

FIG. 3 is an enlarged longitudinal vertical sectional view through a portion of the inhalation system;

FIG. 4 is an enlarged fragmented exploded perspective view illustrating an adatper sleeve for mounting onto a conventional inhaler tube;

FIG. 5 is an enlarged fragmented perspective view, with portions depicted in vertical section, illustrating the inhalation system including the adapter sleeve mounted onto an inhaler tube;

DETAILED DESCRIPTION OF THE PREFERRED EMBODIMENTS

Figure 6:
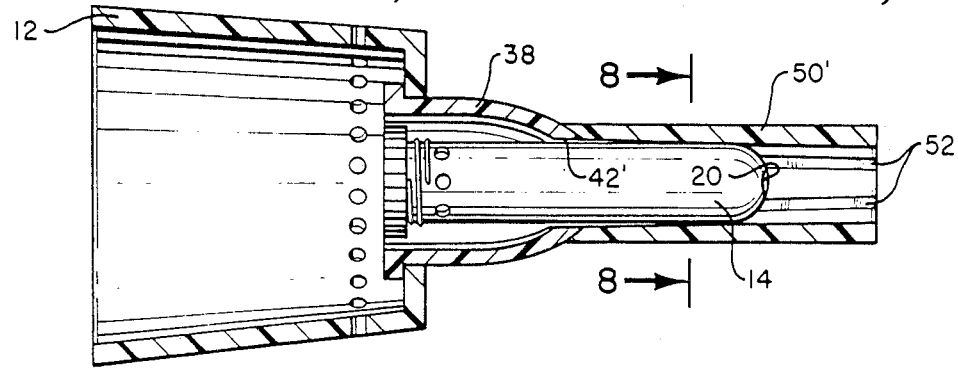
FIG. 6 is an enlarged longitudinal vertical sectional view similar to FIG. 3 but illustrating one alternate embodiment of the invention.

As shown in the exemplary drawings, an improved nasal inhalation system referred to generally by the reference numeral 10 is shown in one preferred form in FIGS. 1-3. The inhalation system 10 includes a mounting base 12 adapted to support an inhaler tube 14 at the discharge end 16 of a portable hand-held air flow source 18 which preferably includes means for heating the air. A flow of air from the source 18 is guided by the mounting base 12 for flow-through passage through the inhaler tube 14 resulting in medicinal vapors which can be directed into a person's nostrils.

The improved nasal inhalation system 10 of the present invention advantageously provides a compact, relatively simple, and relatively inexpensive device for producing medicinal vapors, wherein the system 10 is adapted for use with a conventional medicament-containing nasal inhalation tube 14. The inhalation tube 14 can be mounted quickly and easily upon the mounting base 12 and subsequently removed therefrom when desired without requiring the use of tools, adjustments, or the like. The base 12 supports the inhaler tube 14 for direct flow through passage of air from the source 18 to produce any of a wide variety of medicinal vapors or other selected vapors or fragrances, in accordance with the substance contained within the inhaler tube 14.

More particularly, as shown best in FIG. 3, the inhaler tube 14 is generally conventional in form and construction, such as the nasal inhaler tube marketed by Richardson-Vicks, Inc., Wilton, Conn., under the name VICKS and containing an antihistamine or other medicine for relieving nasal congestion. Alternatively, the inhaler tube 14 can be adapted for carrying other types of medicines designed for nasal inhalation adminstration, including, but not limited to insulin and others.

The inhaler tube conventionally includes an elongated hollow and generally cylindrical geometry having a smoothly rounded forward or downstream end tip 19 terminating with an axially centered exit port 20. The interior of the tube 14 (not shown) is hollow and contains the selected medicament or other substance, as described above. At the opposite end of the tube 14, a series of relatively small inlet ports 22 are formed at a position immediately downstream from an elarged base end 24. As is known in the art, the base end 24 is normally designed to cooperate with a removable cap (not shown) which can be placed over the tube 14 and fastened to the base end as by threads, snap-fitting, or the like, to prevent air flow into or through the inlet ports 22 or the exit port 20 when the inhaler tube is not in use.

The inhalation system 10 of the present invention includes the generally cup-shaped mounting base 12 having an open upstream end with any convenient size and shape to fit securely yet removably onto the downstream discharge end 16 of the air flow source 18. This air flow source, as shown generally in FIG. 1, has an internally mounted motor 100 and fan 102 and heating means 104 for drawing air inwardly into a housing 26 through vents 28 and propelling that air outwardly at the discharge end 16, as viewed by arrows 30 in FIG. 1.

An electrical power cord 32 is provided to supply electrical power to the air source preferably under the control of a rheostat switch 34 to permit close regulation of air flow rate and temperature.

The cup-shaped mounting base 12 terminates at its downstream end in a forward or downstream end wall 36 having a central opening 37 within which is seated a support nozzle 38, preferaby constructed from a somewhat pliable elastomer material. This support nozzle includes, in the preferred form, a radially enlarged upstream end flange 40 appropriately secured to the inboard side of the mounting base end wall 36. From the flange 40, the nozzle 38 protrudes in a forward or downstream direction through the opening 37 with a progressively diminishing diametric cross section and terminates at a forward end defining an axially centered support opening 42. This support opening 42 is sized for press-fit reception of the inhaler tube and conveniently contacts the periphery of the tube 14 at a position downstream from the entry ports 22 when the base end 24 thereof is generally aligned axially with the nozzle flange 40. Importantly, the upstream end of the nozzle is sized to define a circumferential air flow clearance chamber 44 about the base end 24 of the inhaler tube 14, thereby peritting air flow from the source 18 into the chamber 44 within the nozzle 38 disposed about an upstream end region of the inhaler tube 14, incuding the inlet ports 22. The air flow is thus permitted to flow through the inlet ports 22 and further through the interior of the inhaler tube in direct contact with the medicine or the like therein to produce the desired vapors which are discharged forwardly from the inhaler tube through the forward end exit port 20.

In use, the inhaler tube 14 is thus mounted quickly and easily into the nozzle 38 carried by the mounting base 12 by merely pushing the tube 14 forwardly into the downstream end of the nozzle. The mounting base is then quickly and easily secured onto the air flow source 18. The source of air, which is preferably heated to enhance therapeutic effects in many instances, flows into the mounting base 12 and further into the annular nozzle chamber 44 for passage through the inhaler tube 14. The inlet ports 20 of the tube 14 are thus exposed to air flow which passes directly through the tube 14 and exits through the exit port 20 for flow directly into a person's nostrils, when the exit port 20 is held up to the nostril of a person receiving the medication. If desired, and depending upon the flow rate of air from the source 18, vents 45 may be formed in the mouting base 12 to prevent excessive air flow rates through the inhaler tube.

To enhance sanitational use of the system 10, an adapter sleeve 50 can be provided as a separate, conveniently sterilizable item, as viewed in FIGS. 4 and 5. For example, the adapter sleeve 50 can be provided as a disposable prepackaged and presterilized item or, in the alternative, the adpater sleeve may be provided in a separate container (not shown) including an appropriate sterilizing solution, such as alcohol or the like.

The adapter sleeve 50 is shown in one preferred form in FIGS. 4 and 5 to have an elongated generally cylindrical construction designed for press-fit reception over the downstream end tip 19 of the inhaler tube 14 when protruding from the support nozzle 38, as viewed in FIG. 5. The length of the sleeve 50 is sufficient to extend beyond the exit port 20 of the inhaler tube 14, thereby providing a spacer element to prevent direct human contact with the tube 14. Moreover, the inner diameter of the sleeve 50 conveniently includes longitudinally extending recessed channels 52 which permit a portion of the air discharged through the exit port 20 to escape rearwardly without flow into a person's nostril. With this construction, excessive pressure within a person's nasal passages is avoided, since the channels 52 provide a relief or escape as a saftety feature.

Figure 7:
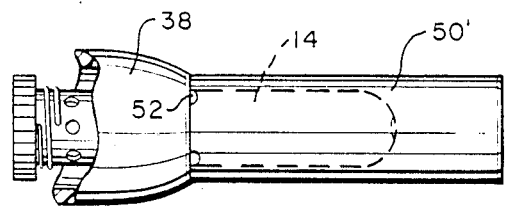
FIG. 7 is a fragmented side elevation view illustrating construction details of the embodiment of FIG. 6.
Figure 8:
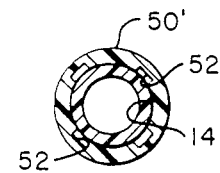
FIG. 8 is a vertical sectional view taken generally on the line 8—8 of FIG. 6.

A modified form of the invention is shown in FIGS. 6-8, wherein a modified adapter sleeve 50' is securely mounted onto the mounting base 12 to provide a combination mounting base/adapter sleeve unit. More particularly, the cup-shaped mounting base 12 includes the forward support nozzle 38, as previously described, except that the nozzle 38 includes a downstream end support opening 42' sized somewhat larger than the body of an inhaler tube 14 of average size. The modified adapter sleeve is secured onto the nozzle 38 as by use of an adhesive or the like to project forwardly therefrom beyond the exit port 20 of the inhaler tube. The inner diameter of the sleeve 50' tapers with diminishing cross-sectional size in a forward direction and includes the enlarged interior channels 52, as previously described.

In use, the tapered bore of the adapter sleeve 50' advantageously fits snugly with different sizes of inhaler tubes, thereby not requiring inhaler tubes of a single standard size. The tube 14 is insertable quickly and easily in the manner described with respect to FIGS. 1-3, after which the mounting base 12 is fitted onto an air flow source as depicted in FIG. 1.

Figure 9:
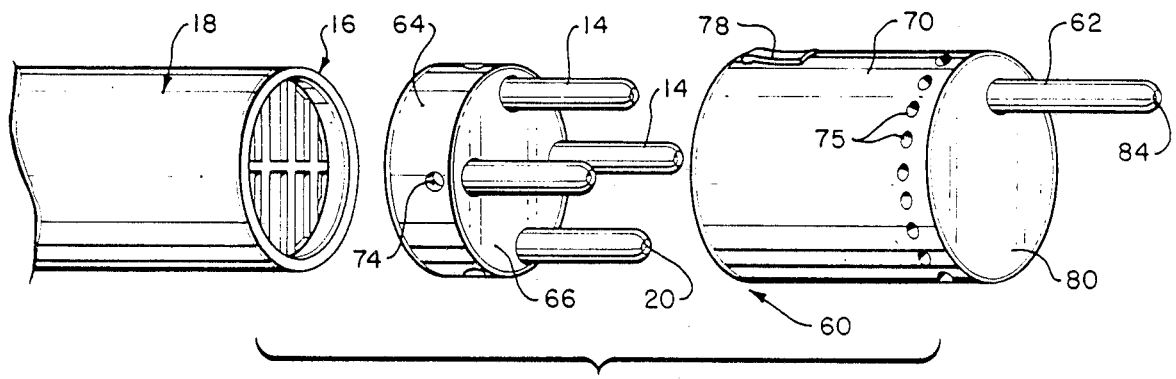
FIG. 9 is a fragmented perspective view illustrating another alternative preferred form of the invention and including multiple inhaler tubes incorporated into a turret assembly.
Figure 10:
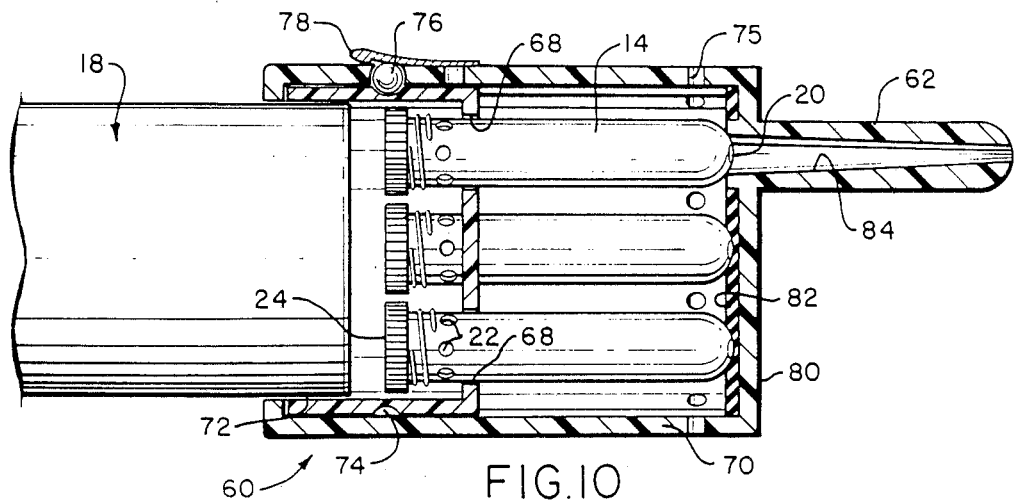
FIG. 10 is an enlarged fragmented vertical sectional view illustrating the turret assembly of FIG. 9.

Another modified form of the invention is shown in FIGS. 9 and 10, wherein a turret assembly 60 is provided for mounting a plurality of medicament-containing inhaler tubes 14 onto the discharge end of an air flow source 18. With this embodiment, different medicines and/or different fragrances contained within the individual inhaler tubes 14 can be selectively aligned with a forwardly protruding open discarge tube 62 thereby delivering medicinal or scented vapors to a person's nostrils, or into a room, etc.

More specifically, the turret assembly 60 comprises a generally cup-shaped mounting base 64 having an open upstream end for appropriate removable connection in any convenient manner onto the discharge end of the air source 18. A forward or downstream end wall 66 of the mounting base 64 is interrupted by an annularly arranged plurality of openings 68 for individual reception of the inhaler tubes 14, all having a construction generally in accordance with the inhaler tube described previously herein with repsect to FIGS. 1-3.

A generally cup-shaped turret cap 70 is sized for close fit sliding reception of an upstream open end thereof over the mounting base 64 to position a short locking flange 72 on the cap beyond the upstream end of the mounting base. Shallow detents 74 on the periphery of the base 64 are provided in an angularly spaced number corresponding with the number of inhaler tubes 14 for receiving a detent ball 76 pressed into an aligned one of the detents 74 by a spring 78. Accordingly, the turret cap 70 can be rotated or indexed in steps about the mounting base 64 to one of a plurality of indexed positions indicated by seating of the index ball 76 in one of the detents 74. Vents 75 may also be formed in the cap 70.

As shown best in FIG. 10, the longitudinal dimensions of the turret cap 70 are chosen for seated contact of the downstream end tips of the inhaler tubes against a forward end wall 80 of the turret cap with the inlet ports 22 of each inhaler disposed upstream relative to the forward end wall 66 of the mounting base 64. With this construction, air from the air source 18 may flow uninterrupted into each of the inhalers through the inlet ports 22. However, for any given indexed position, all but one of the inhaler tubes have their downstream end tips seated against a seal 82 at the inboard side of the end wall 80, with the remaining single inhaler tube having its exit port 20 aligned with a discharge passage 84 in the open discharge tube 62.

Accordingly, the turret assembly 60 can be adjusted before or during operation of the air source 18 to align a selected one of the inhaler tubes 14 with the discharge tube 62, thereby limiting air flow passage to a selected one of the inhaler tubes. An alternative inhaler tube may be quickly and easily selected by mere index rotation of the turret cap to provide alternate selected medicinal vapors, fragrances, or the like. If desired, the adatper sleeve 50, as shown in FIGS. 4 and 5 may be mounted on the discharge tube 62 to prevent direct human contact therewith during use.

The present invention thus provides a relatively simple yet highly versatile nasal inhalation system adapted for use with one or more conventional inhaler tubes. Such inhaler tubes of the same or different sizes may be interchanged quickly and easily as required. Moreover, when combined with the air flow source, it has been found that the life of the inhaler tube is exended due to more efficient withdrawing of vapors in comparison with conventional use.

A variety of modifications and improvements to the nasal inhalation system described herein are believed to be apparent to those skilled in the art. Accordingly, no limitation on the invention is intended by way of the description and drawings, except as set forth in the appended claims.

What is claimed is:

1. A nasal inhalation system, comprising:
   a power-driven heated air flow source;
   a medicament-containing inhaler tube having at least one entry port and at least one exit port generally at opposite ends thereof;
   a support nozzle including means for removably supporting said inhaler tube at a position between said entry and exit ports and without obstructing said entry and exit ports, said support nozzle defining an air flow clearance chamber generally circumferentially about the end of said inhaler tube having said entry port therein; and
   means for mounting said support nozzle onto said air flow source with said inhaler tube supported by said support nozzle in a position for flow-through passage of air from said air flow source into said entry port and through said inhaler tube for discharge via said exit port.

2. The nasal inhalation system of claim 1 wherein said support nozzle has a diametric cross-sectional size diminishing from an upstream end substantially larger than the diametric size of said tube to a downstream end thereof, said downstream end of said nozzle defining an opening, said inhaler tube being slidably supported with press-fit reception within said downstream end opening.

3. The nasal inhalation system of claim 2 wherein said at least one entry port in said inhaler tube is formed therein a short distance from the upstream end of said tube, said support nozzle being sized and shaped to support said tube at a position downstream relative to said entry port when said upstream tube end and said upstream nozzle end are generally aligned axially with each other, said upstream end of said tube being substantially closed by a cap.

4. The nasal inhalation system of claim 1 wherein said mounting means comprises a generally cup-shaped mounting base having an open upstream base end and including means for removable connection of said open upstream base end to said air flow source, said nozzle being supported by said mounting base.

5. The nasal inhalation system of claim 4 wherein said mounting base is vented.

6. The nasal inhalation system of claim 1 further including an adapter sleeve at a downstream end region of said inhaler tube when said inhaler tube is supported by said support nozzle, said adapter sleeve being supported about said tube and projecting in a downstream direction beyond the downstream end region thereof for spacing the exit port region of said inhaler tube from direct human contact during use.

7. The nasal inhalation system of claim 6 wherein said adapter sleeve is mounted fixedly onto said support nozzle.

8. A nasal inhalation system for mounting onto a source of air flow, comprising:
  an inhaler tube having at least one entry port near a first end thereof and at least one exit port generally at a second end thereof, said first end being substantially closed by a cap and said entry port being formed in said tube in axially spaced relation to said cap;
  a support nozzle including means for removably supporting said inhaler tube at a position between said entry and exit ports and without obstructing said entry and exit ports, said support nozzle defining an air flow clearance chamber generally circumferentially about said tube first end, said chamber being open to said entry port and open in an upstream direction away from said tube second end; and
  means for mounting said support nozzle onto said air flow source with said inhaler tube supported by said nozzle in a position for flow-through passage of air from the air flow source into said chamber and further into said entry port and through said inhaler tube for discharge via said exit port.

9. The nasal inhalation system of claim 8 wherein said support nozzle has a diametric cross-sectional size diminishing from an upstream substantially larger than the diametric size of said tube to a downstream end thereof, said downstream end of said nozzle defining an opening, said inhaler tube being slidably supported with press-fit reception into said downstream end opening.

10. The nasal inhalation system of claim 9 wherein said at least one entry port in said inhaler tube is formed therein a short distance from the upstream end of said tube, said support nozzle being sized and shaped to support said tube at a position downstream relative to said entry port when said upstream tube end and said upstream nozzle end are generally aligned axially with each other.

11. The nasal inhalation system of claim 9 wherein said mounting means comprises a generally cup-shaped mounting base having an open upstream base end and including means for removable connection of said open upstream base end to the air flow source, said nozzle being supported by said mounting base.

12. The nasal inhalation system of claim 8 further including an adapter sleeve at a downstream end region of said inhaler tube when said inhaler tube is supported by said support nozzle, said adapter sleeve being supported about said tube and projecting in a downstream direction beyond said downstream end region thereof for spacing the exit port region of said inhaler tube from direct human contact during use.

13. The nasal inhalation system of claim 12 wherein said adapter sleeve is mounted fixedly onto said support nozzle.

14. The nasal inhalation system of claim 12 wherein said adapter sleeve has an internal bore of tapered cross-sectional size decreasing toward the downstream end of said adapter sleeve, a portion of said adapter sleeve intermediate its opposite ends engaging said tube in substantially press-fit relation.

15. A nasal inhalation system, comprising:
  an air flow source;
  an inhaler tube having at least one entry port and at least one exit port generally at opposite ends thereof;
  a support nozzle including means for removably supporting said inhaler tube at a position between said entry and exit ports and without obstructing said entry and exit ports;
  means for mounting said support nozzle onto said air flow source with said inhaler tube supported by said nozzle in a position for flow-through passage of air from said air flow source into said entry port and through said inhaler tube for discharge via said exit port; and
  an adapter sleeve having an internal bore sized for relatively close reception about a downstream end region of said inhaler tube when said inhaler tube is supported by said support nozzle, said adapter sleeve projecting in a downstream direction beyond said downstream end region of said inhaler tube to space the exit port region of said inhaler tube from direct human contact during use, said adapter sleeve having a primary opening for discharge of a portion of the air flow from the exit port and further defining at least one vent opening for additional discharge of another portion of the air flow from the exit port.

16. The nasal inhalation system of claim 15 wherein said primary opening in said adapter sleeve opens in a first direction for directing a portion of the air flow into a person's nasal passage, said vent opening being formed to open in a second, different direction.

17. A nasal inhalation system, comprising:
  a power-driven heated air flow source;
  a medicament-containing inhaler tube having at least one entry port and at least one exit port generally at opposite ends thereof;
  a generally cup-shaped mounting base having an open upstream base end and including means for removable connection to said air flow source, said mounting base further including a downstream end having an opening formed therein; and
  a support nozzle seated within said downstream end opening of said mounting base, said support nozzle having a cross-sectional size diminishing from an upstream end which is substantially larger than the cross-sectional size of said inhaler tube to a downstream end of said support nozzle which defines an opening for substantially press-fit reception of said inhaler tube;
  said inhaler tube being sidably removably seated within said downstream end opening of said support nozzle at a position along said tube generally between said entry and exit ports, said support nozzle defining an air flow clearance chamber about an upstream end region of said inhaler tube, whereby the air flow from said air flow source passes through said mounting base to said support nozzle for further passage through said inhaler tube via said entry and exit ports and for discharge from said exit port into a person's nasal passages.

18. The nasal inhalation system of claim 17 further including a hollow adapter sleeve positioned about a downstream end region of said inhaler tube when said inhaler tube is seated within said support nozzle, said sleeve projecting in a downstream direction beyond said inhaler tube to space said inhaler tube from direct human contact during use.

19. The nasal inhalation system of claim 18 wherein said sleeve is removably mounted on said tube.

20. The nasal inhalation system of claim 18 wherein said sleeve is fixed to said support nozzle.

21. The nasal inhalation system of claim 17 wherein said mounting base has at least one vent opening formed therein to permit a portion of the air flow therethrough to escape without passage through said inhaler tube.

22. A nasal inhalation system, comprising:
a power-driven heated air flow source;
an inhaler tube having at least one entry port and at least one exit port generally at opposite ends thereof;
a generally cup-shaped mounting base having an open upstream base end and including means for removable connection to said air flow source, said mounting base further including a downstream end having an opening formed therein; and
a support nozzle seated within said downstream end opening of said mounting base, said support nozzle having a cross-sectional size diminishing from an upstream end which is substantially larger than the cross-sectional size of said inhaler tube to a downstream end of said support nozzle which defines an opening for substantially press-fit reception of said inhaler tube;
said inhaler tube being slidably removably seated within said downstream end opening of said support nozzle at a position along said tube generally between said entry and exit ports, said support nozzle defining an air flow clearance chamber about an upstream end region of said inhaler tube, whereby the air flow from said air flow source passes through said mounting base to said support nozzle for further passage through said inhaler tube via said entry and exit ports and for discharge from said exit port into a person's nasal passages;
said inhaler tube further having a substantially closed cap at the upstream end thereof, said entry port being formed in said inhaler tube at a position spaced axially in a downstream direction a short distance from said cap, said entry port being open to said air flow clearance chamber.

23. A nasal inhalation system, comprising:
a power-driven heated air flow source;
an inhaler tube having at least one entry port and at least one exit port generally at opposite ends thereof;
a generally cup-shaped mounting base having an open upstream base end and including means for removable connection to said air flow source, said mounting base further including a downstream end having an opening formed therein;
a support nozzle seated within said downstream end opening of said mounting base, said support nozzle having a cross-sectional size diminishing from an upstream end which is substantially larger than the cross-sectional size of said inhaler tube to a downstream end of said support nozzle which defines an opening for substantially press-fit reception of said inhaler tube;
said inhaler tube being slidably removably seated within said downstream end opening of said support nozzle at a position along said tube generally between said entry and exit ports, said support nozzle defining an air flow clearance chamber about an upstream end region of said inhaler tube, whereby the air flow from said air flow source passes through said mounting base to said support nozzle for further passage through said inhaler tube via said entry and exit ports and for discharge from said exit port into a person's nasal passages; and
a hollow adapter sleeve positioned about a downstream end region of said inhaler tube when said inhaler tube is seated within said support nozzle, said sleeve projecting in a downstream direction beyond said inhaler tube to space said inhaler tube from direct human contact during use;
said sleeve defining an open bore for reception about the downstream end region of said inhaler tube, said open bore being lined by longitudinally extending recessed channels, said channels permitting a portion of the air flow discharged from said exit port to escape through said channels in a direction away from a person's nasal passages.

* * * * *